(12) United States Patent
Bedingham et al.

(10) Patent No.: US 8,128,893 B2
(45) Date of Patent: Mar. 6, 2012

(54) THERMAL TRANSFER METHODS AND STRUCTURES FOR MICROFLUIDIC SYSTEMS

(75) Inventors: William Bedingham, Woodbury, MN (US); Christopher R. Kokaisel, St. Paul, MN (US); Jeffrey C. Pederson, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1109 days.

(21) Appl. No.: 11/962,703

(22) Filed: Dec. 21, 2007

(65) Prior Publication Data
US 2008/0149190 A1    Jun. 26, 2008

Related U.S. Application Data

(60) Provisional application No. 60/871,611, filed on Dec. 22, 2006.

(51) Int. Cl.
*B01L 7/00* (2006.01)
(52) U.S. Cl. ......... 422/504; 422/502; 422/503; 422/506
(58) Field of Classification Search .................. 422/502, 422/503, 504, 506
See application file for complete search history.

(56) References Cited

U.S. PATENT DOCUMENTS

| | | |
|---|---|---|
| 3,555,284 A | 1/1971 | Anderson |
| 3,595,386 A | 7/1971 | Hradel |
| 3,795,451 A | 3/1974 | Mailen |
| 3,798,459 A | 3/1974 | Anderson et al. |
| 3,873,217 A | 3/1975 | Anderson et al. |
| 4,030,834 A | 6/1977 | Bauer et al. |
| 4,244,916 A | 1/1981 | Guigan |
| 4,396,579 A | 8/1983 | Schroeder et al. |
| 4,632,908 A | 12/1986 | Schultz |
| 4,906,432 A | 3/1990 | Geiselman |
| 5,049,591 A | 9/1991 | Hayashi et al. |
| 5,128,197 A | 7/1992 | Kobayashi et al. |
| 5,135,786 A | 8/1992 | Hayashi et al. |

(Continued)

FOREIGN PATENT DOCUMENTS

DE    37 12 624    11/1988

(Continued)

OTHER PUBLICATIONS

*Handbook of Pressure Sensitive Adhesive Technology*, Donatas Satas (Ed.) $2^{nd}$ Edition, p. 172, and Fig. 8-16 on p. 173, Van Nostrand Reinhold, New York, NY, (1989).
*Handbook of Pressure Sensitive Adhesive Technology*, $3^{rd}$ Edition, p. 508-549 (1999).
Sambrook et al., *Molecular Cloning, A Laboratory Manual*, $2^{nd}$ Edition, Cold Spring Harbor Laboratory, (1989).

(Continued)

*Primary Examiner* — Yelena G Gakh
*Assistant Examiner* — Christopher A Hixson
(74) *Attorney, Agent, or Firm* — Nicole J. Einerson

(57) ABSTRACT

Processing devices that include one or more process arrays with thermal transfer structures that can be used alone or in conjunction with gravity/rotation to transport fluids within a microfluidic system. The thermal transport function can be accomplished by changing the temperature of one or more chambers to create a vacuum to draw fluids in selected directions within the process array. The methods and apparatus of the present invention may provide the ability to move fluids in a direction that is against the direction of gravity or any centrifugal forces generated by rotating a processing device using the thermal transfer structures. In other words, fluids may be moved against the direction of gravity or towards the axis of rotation using the thermally-activated vacuum.

13 Claims, 8 Drawing Sheets

U.S. PATENT DOCUMENTS

| | | | |
|---|---|---|---|
| 5,139,832 | A | 8/1992 | Hayashi et al. |
| 5,145,935 | A | 9/1992 | Hayashi |
| 5,173,262 | A * | 12/1992 | Burtis et al. ............... 422/72 |
| 5,278,377 | A | 1/1994 | Tsai |
| 5,429,810 | A | 7/1995 | Knaepler et al. |
| 5,446,270 | A | 8/1995 | Chamberlain et al. |
| 5,461,134 | A | 10/1995 | Leir et al. |
| 5,496,520 | A | 3/1996 | Kelton et al. |
| 5,529,708 | A | 6/1996 | Palmgren et al. |
| 5,536,475 | A | 7/1996 | Moubayed et al. |
| 5,550,228 | A | 8/1996 | Godiard |
| 5,571,410 | A | 11/1996 | Swedberg et al. |
| 5,593,838 | A | 1/1997 | Warner et al. |
| 5,604,130 | A | 2/1997 | Zanzucchi et al. |
| 5,637,469 | A | 6/1997 | Wilding et al. |
| 5,639,428 | A | 6/1997 | Cottingham |
| 5,639,810 | A | 6/1997 | Smith, III et al. |
| 5,693,233 | A | 12/1997 | Schembri |
| 5,700,695 | A | 12/1997 | Yassinzadeh et al. |
| 5,720,923 | A | 2/1998 | Haff et al. |
| 5,721,123 | A | 2/1998 | Hayes et al. |
| 5,800,785 | A | 9/1998 | Bochner |
| 5,819,842 | A | 10/1998 | Potter et al. |
| 5,822,903 | A | 10/1998 | Davis, Sr. |
| 5,863,502 | A | 1/1999 | Southgate et al. |
| 5,863,708 | A * | 1/1999 | Zanzucchi et al. ............ 506/23 |
| 5,869,002 | A | 2/1999 | Limon et al. |
| 5,882,774 | A | 3/1999 | Jonza et al. |
| 5,925,455 | A | 7/1999 | Bruzzone et al. |
| 5,948,227 | A | 9/1999 | Dubrow |
| 6,007,914 | A | 12/1999 | Joseph et al. |
| 6,013,513 | A | 1/2000 | Reber et al. |
| 6,030,581 | A | 2/2000 | Virtanen |
| 6,063,589 | A | 5/2000 | Kellogg et al. |
| 6,093,370 | A | 7/2000 | Yasuda et al. |
| 6,101,032 | A | 8/2000 | Wortman et al. |
| 6,143,248 | A | 11/2000 | Kellogg et al. |
| 6,319,469 | B1 | 11/2001 | Mian et al. |
| 6,414,136 | B1 | 7/2002 | Spicer et al. |
| 6,467,275 | B1 | 10/2002 | Ghoshal |
| 6,527,432 | B2 | 3/2003 | Kellogg et al. |
| 6,558,947 | B1 | 5/2003 | Lund et al. |
| 6,565,808 | B2 | 5/2003 | Hudak et al. |
| 6,572,830 | B1 | 6/2003 | Burdon et al. |
| 6,582,662 | B1 | 6/2003 | Kellogg et al. |
| 6,617,136 | B2 | 9/2003 | Parthasarathy et al. |
| 6,627,159 | B1 | 9/2003 | Bedingham et al. |
| 6,648,853 | B1 | 11/2003 | McEntee |
| 6,660,147 | B1 | 12/2003 | Woudenberg et al. |
| 6,709,869 | B2 | 3/2004 | Mian et al. |
| 6,720,187 | B2 | 4/2004 | Bedingham et al. |
| 6,734,401 | B2 | 5/2004 | Bedingham et al. |
| 6,972,113 | B1 | 12/2005 | Ramshaw et al. |
| 6,987,253 | B2 | 1/2006 | Bedingham et al. |
| 7,164,107 | B2 | 1/2007 | Bedingham et al. |
| 7,435,933 | B2 | 10/2008 | Bedingham et al. |
| 2002/0047003 | A1 | 4/2002 | Bedingham et al. |
| 2002/0048533 | A1 | 4/2002 | Harms et al. |
| 2002/0064885 | A1 | 5/2002 | Bedingham et al. |
| 2003/0118804 | A1 | 6/2003 | Bedingham et al. |
| 2003/0138779 | A1 | 7/2003 | Parthasarathy et al. |
| 2003/0231878 | A1 | 12/2003 | Shigeura |
| 2004/0007275 | A1 | 1/2004 | Hui Liu et al. |
| 2004/0016898 | A1 | 1/2004 | Cox et al. |
| 2004/0018117 | A1 | 1/2004 | Desmond et al. |
| 2004/0053290 | A1 | 3/2004 | Terbrueggen et al. |
| 2004/0191125 | A1 | 9/2004 | Kellogg et al. |
| 2005/0041525 | A1 | 2/2005 | Pugia et al. |
| 2005/0109396 | A1 | 5/2005 | Zucchelli et al. |
| 2005/0126312 | A1 | 6/2005 | Bedingham et al. |
| 2005/0129583 | A1 | 6/2005 | Bedingham et al. |
| 2005/0130177 | A1 | 6/2005 | Bedingham et al. |
| 2005/0142663 | A1 | 6/2005 | Parthasarathy et al. |
| 2005/0224337 | A1 | 10/2005 | Iwasaki et al. |
| 2005/0277195 | A1 | 12/2005 | Holmquist et al. |
| 2006/0040273 | A1 | 2/2006 | Chaiken et al. |
| 2006/0076346 | A1 | 4/2006 | Bedingham et al. |
| 2007/0007270 | A1 | 1/2007 | Bedingham et al. |
| 2007/0009391 | A1 | 1/2007 | Bedingham et al. |
| 2007/0010007 | A1 | 1/2007 | Aysta et al. |
| 2008/0314895 | A1 | 12/2008 | Bedingham |

FOREIGN PATENT DOCUMENTS

| | | |
|---|---|---|
| EP | 0 169 306 | 1/1986 |
| EP | 0 693 560 | 1/1996 |
| EP | 0 807 468 | 11/1997 |
| EP | 0 810 030 | 12/1997 |
| EP | 0 965 388 | 12/1999 |
| EP | 1 681 553 | 7/2006 |
| JP | 60-238745 | 11/1985 |
| JP | 63-019558 | 1/1988 |
| JP | 64-041861 | 2/1989 |
| JP | 2292720 | 12/1990 |
| JP | 3-048770 | 3/1991 |
| JP | 5-093729 | 4/1993 |
| JP | 5-507878 | 11/1993 |
| JP | 6-050981 | 2/1994 |
| JP | 9-189704 | 7/1997 |
| JP | 10-019884 | 1/1998 |
| WO | WO 94/29400 | 2/1994 |
| WO | WO 95/18676 | 7/1995 |
| WO | WO 96/34028 | 10/1996 |
| WO | WO 96/34029 | 10/1996 |
| WO | WO 96/35458 | 11/1996 |
| WO | WO 96/41864 | 12/1996 |
| WO | WO 96/41865 | 12/1996 |
| WO | WO 97/21090 | 6/1997 |
| WO | WO 97/46707 | 12/1997 |
| WO | WO 98/07019 | 2/1998 |
| WO | WO 98/49340 | 11/1998 |
| WO | WO 98/50147 | 11/1998 |
| WO | WO 98/53311 | 11/1998 |
| WO | WO 99/09394 | 2/1999 |
| WO | WO 99/36248 | 7/1999 |
| WO | WO 99/36258 | 7/1999 |
| WO | WO 99/36809 | 7/1999 |
| WO | WO 99/36810 | 7/1999 |
| WO | WO 99/36812 | 7/1999 |
| WO | WO 99/55827 | 11/1999 |
| WO | WO 99/58245 | 11/1999 |
| WO | WO 99/67639 | 12/1999 |
| WO | WO 00/05582 | 2/2000 |
| WO | WO 00/35583 | 6/2000 |
| WO | WO 00/40750 | 7/2000 |
| WO | WO 00/50172 | 8/2000 |
| WO | WO 00/50642 | 8/2000 |
| WO | WO 00/68336 | 11/2000 |
| WO | WO 00/69560 | 11/2000 |
| WO | WO 00/78455 | 12/2000 |
| WO | WO 00/79285 | 12/2000 |
| WO | WO 01/07892 | 2/2001 |
| WO | WO 01/25490 | 4/2001 |
| WO | WO 01/25491 | 4/2001 |
| WO | WO 03/104783 | 12/2003 |
| WO | WO 2004/011143 | 2/2004 |
| WO | WO 2004/011147 | 2/2004 |
| WO | WO 2004/011365 | 2/2004 |
| WO | WO 2004/011681 | 2/2004 |
| WO | WO 2005/005045 | 1/2005 |
| WO | WO 2005/028096 | 3/2005 |
| WO | WO 2005/079986 | 9/2005 |

OTHER PUBLICATIONS

*Test Methods for Pressure Sensitive Adhesive Tapes*, 12th Edition, Pressure Sensitive Tape Council, (1996).
U.S. Appl. No. 60/237,072 filed Oct. 2, 2000, titled Sample Processing Devices, Systems and Methods.
U.S. Appl. No. 60/284,637 filed Apr. 18, 2001, titled Enhanced Sample Processing Devices, Systems and Methods, abandoned.
U.S. Appl. No. 60/260,063 filed Jan. 6, 2001, titled Sample Processing Devices, Systems and Methods, abandoned.
U.S. Appl. No. 11/962,669, filed Dec. 21, 2007, title Enhanced Sample Processing Devices, Systems and Methods.

* cited by examiner

THERMAL TRANSFER METHODS AND STRUCTURES FOR MICROFLUIDIC SYSTEMS

CROSS REFERENCE TO RELATED APPLICATIONS

The present application claims the benefit under 35 U.S.C. §119(e) of U.S. Provisional Patent Application No. 60/871,611, titled THERMAL TRANSFER METHODS AND STRUCTURES FOR MICROFLUIDIC SYSTEMS, filed Dec. 22, 2006, which is hereby incorporated by reference in its entirety.

BACKGROUND

The present invention relates to the field of microfluidic processing devices. More particularly, the present invention provides methods and devices that employ thermally-activated vacuum to move analyte within a microfluidic process array.

Devices in which various chemical or biological processes are performed play an increasing role in scientific and/or diagnostic investigations. The chambers provided in such devices are preferably small in volume to reduce the amount of analyte required to perform the processes.

One persistent issue associated with processing devices including chambers is in the transfer of fluids between different features in the devices. Conventional approaches to transferring fluidic contents between chambers have often required human intervention (e.g., manual pipetting) and/or robotic manipulation. Such transfer processes suffer from a number of disadvantages including, but not limited to, the potential for errors, complexity and associated high costs, etc.

SUMMARY OF THE INVENTION

The present invention provides processing devices that include one or more process arrays with thermal transfer structures that can be used alone or in conjunction with rotation to transport fluids within a microfluidic system. The thermal transport function can be accomplished by changing the temperature of one or more chambers to create a vacuum to draw fluids in selected directions within the process array.

Among the potential advantages of the methods and apparatus of the present invention are the ability to move fluids in a direction that is against the direction of gravitational forces and/or centrifugal forces generated by rotating a processing device using the thermal transfer structures. In other words, fluids may be moved against the force of gravity or towards an axis of rotation using the thermally-activated vacuum. As used herein, the term "vacuum" refers to a pressure differential between volumes in a process array large enough to move fluids in a selected direction.

The thermal transfer structure may also be used to control fluid movement within the processing device without the need for physical valve structures that require opening or closing of physical structures to allow for fluid passage. For example, the dimensions, geometry, materials, etc., may be selected such that fluid passage will not typically occur in the absence of a vacuum. One feature that may be used is a conduit that includes a fluid trap as described herein. In such instances, the thermally-activated vacuum provided by a thermal transfer structure can be used to control fluid movement within a process array.

In some embodiments, the thermal transfer structure can include a thermal drive chamber located in an area of the processing device that is remote from the chambers between which fluid is to be transported. The remote thermal drive chamber can be fluidly connected to the chambers between which fluid is to be transported by a conduit formed in the device. One potential advantage of such a structure is that the portion of the processing device heated (or cooled) to create the vacuum may be sufficiently removed from the chambers between which fluid is to be transported such that the analytes in the transported fluids are not significantly heated or cooled as a result of the heating or cooling of the thermal drive chamber.

Thermal transfer structures and methods may also be used to transport multiple discrete volumes of fluids (sequentially and/or simultaneously) into or through a chamber in a process array. Such control over fluid transport can be used for, e.g., washing to remove unwanted materials from a sample, delivery of reagents at selected times and in selected amounts, etc. When used to transfer multiple discrete volumes of fluids, the thermal transfer structures may operate more effectively due to the presence of liquids in the thermal drive chambers where at least a portion of the liquid changes phase to become a gas. Such phase changes may increase the volumetric changes in the resident fluid caused by heating and, thus, the resulting vacuum force may also increase as the resident fluid is cooled.

In one aspect, the present invention provides a method for transferring fluid within a processing device by providing a processing device having at least one process array that includes a first chamber and thermal transfer structure containing resident fluid, wherein the thermal transfer structure includes a transfer conduit connected to the first chamber; providing analyte in the first chamber; passing a first portion of the resident fluid through the transfer conduit into the analyte in the first chamber by heating at least a portion of the resident fluid in the thermal transfer structure such that the volume of the resident fluid within the thermal transfer structure increases to force the first portion of the resident fluid into the first chamber; and cooling the heated resident fluid in the thermal transfer structure after passing the first portion of the resident fluid into the first chamber, wherein the volume of the resident fluid within the thermal transfer structure decreases such that at least a portion of the analyte in the first chamber is drawn into the thermal transfer structure through the transfer conduit.

Methods of the present invention may optionally include performing two or more sequential heating and cooling cycles on the resident fluid in the thermal transfer structure.

Methods of the present invention may optionally include rotating the processing device about an axis of rotation while passing the first portion of the resident fluid through the analyte in the first chamber, wherein the rotating drives the analyte towards a radially distal end of the first chamber. During rotating, the methods may further include rotating such that at least a portion of the transfer conduit is located closer to the axis of rotation than at least a portion of the first chamber.

Methods of the present invention may involve a thermal transfer structure that includes a trap chamber in fluid communication with the transfer conduit, and wherein the thermal transfer structure includes a thermal drive chamber in fluid communication with the trap chamber through a drive conduit, and further wherein the portion of the analyte drawn into the thermal transfer structure through the transfer conduit is deposited in the trap chamber. The resident fluid in the trap chamber may not be directly heated. The transfer conduit and the drive conduit may connect to the trap chamber on a radially proximal side of the trap chamber, such that fluids entering the trap chamber while rotating the processing device are driven towards a radially distal side of the trap chamber such that a majority of the fluids entering the trap chamber do not enter the drive conduit (wherein substantially all of the liquids entering the trap chamber may not enter the drive conduit). The methods may involve rotating the processing device about an axis of rotation, wherein the radially proximal side of the trap chamber is located closer to the axis of rotation than the radially distal side of the trap chamber.

In some methods, the transfer conduit may connect to the first chamber at a first port, wherein the first port is located at an intermediate location along a radial length occupied by the first chamber, wherein the radial length is determined along a radius extending along a radius extending from the axis of rotation of a rotating processing device.

Some methods may include opening a valve located between the first chamber and the transfer conduit before passing a first portion of the resident fluid through the transfer conduit into the analyte.

The process array may include a second chamber and second conduit extending between the second chamber and the first chamber, wherein the method further includes delivering fluid from the second chamber to the first chamber through the second conduit by rotating the processing device about an axis of rotation. The method may further include opening a second chamber valve located between the second chamber and the second conduit before delivering fluid from the second chamber to the first chamber through the second conduit. The processing device may further include an intermediate chamber located between the second chamber and the first chamber along the second conduit, wherein the fluid delivered to the first chamber from the second chamber passes into the intermediate chamber before the fluid reaches the first chamber, wherein the intermediate chamber includes a reagent located therein, and wherein the fluid contacts the reagent in the intermediate chamber before reaching the first chamber. Methods of the present invention may include opening an intermediate chamber inlet valve located between the intermediate chamber and the second chamber before passing the fluid from the second chamber into the intermediate chamber. The methods may further include opening an intermediate chamber outlet valve located between the intermediate chamber and the first chamber before passing the fluid from the intermediate chamber to the first chamber.

In another aspect, the present invention may provide a processing device that includes at least one process array formed in a body, wherein the at least one process array includes a first chamber; a second chamber; and a process conduit extending between the first chamber and the second chamber, wherein the first chamber and the second chamber define an upstream direction when moving from the second chamber towards the first chamber and a downstream direction when moving from the first chamber towards the second chamber. The process array further includes thermal transfer structure including a thermal drive chamber containing resident fluid and a transfer conduit extending between the first chamber and the thermal drive chamber, wherein the transfer conduit enters the first chamber through a transfer port, and wherein the transfer conduit comprises a fluid trap in which a portion of the transfer conduit travels in the upstream direction between the transfer port and the thermal drive chamber.

In some devices, the fluid trap of the transfer conduit reaches at least a midpoint of the first chamber between the first chamber and the thermal drive chamber.

In some devices, a valve is located between the first chamber and the thermal drive chamber, wherein fluid passage between the first chamber and the thermal drive chamber through the transfer conduit is prevented until the valve is opened.

In some devices, the thermal transfer structure further includes a trap chamber located along the transfer conduit between the first chamber and the thermal drive chamber, wherein the trap chamber is located within the fluid trap or between the fluid trap and the thermal drive chamber.

In some devices, the trap chamber is connected to the transfer conduit along an upstream end of the trap chamber.

In some devices, the thermal transfer structure includes two or more thermal drive chambers, wherein all of the two or more thermal drive chambers are located downstream of the fluid trap in the transfer conduit. A valve may be located between the first chamber and each of the thermal drive chambers, wherein fluid passage between the first chamber and each of the thermal drive chambers through the transfer conduit is prevented until the valve located between the first chamber and the thermal drive chamber is opened.

In some devices, the process conduit connects to the first chamber in a direction downstream from the transfer port.

In some devices, a valve is located between the first chamber and the process conduit, wherein fluid passage from the first chamber to the second chamber through the process conduit is prevented until the valve is opened.

In some devices, a plurality of the process arrays are located in the body, wherein the process arrays are substantially radially aligned about a center of the body such that the upstream and downstream directions extend substantially radially from the center of the body.

These and other features and advantages of the present invention are described below in connection with various illustrative embodiments of the devices and methods of the present invention.

DETAILED DESCRIPTION OF EXEMPLARY EMBODIMENTS OF THE INVENTION

Figure 1:
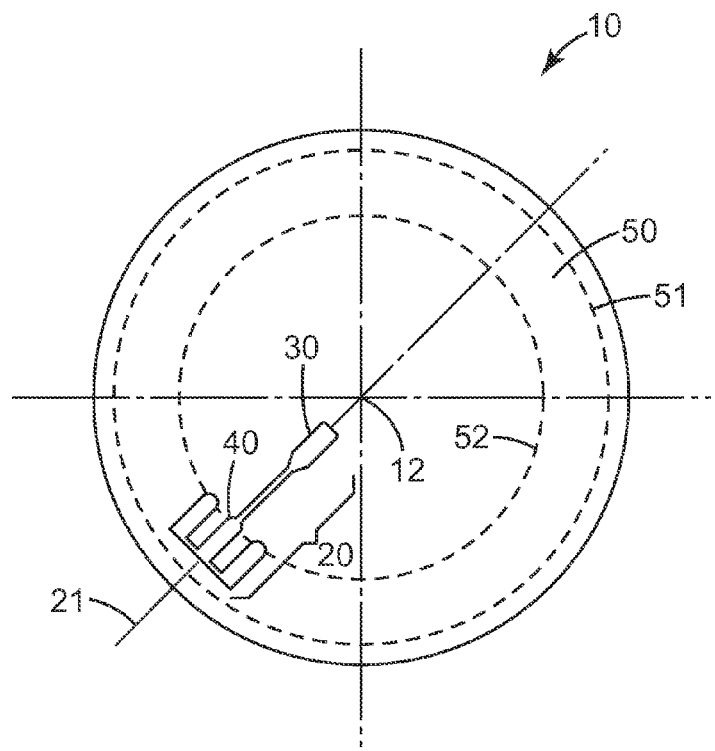
FIG. 1 is a plan view of one exemplary processing device according to the present invention.

In the following detailed description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides a processing device that can be used in the processing of an analyte. The analyte itself may be in the form of a fluid (e.g., a solution, etc.), or the analyte may be in the form of a solid or semi-solid material carried in a fluid. The analyte may be entrained in the fluid, in solution within the fluid, etc. For simplicity, the term "analyte" will be used herein to refer to any fluid in which the analyte is or may be located—regardless of whether the analyte is, itself, a fluid or is contained within a carrier fluid (in solution, suspension, etc.). Furthermore, in some instances, analyte may be used to refer to fluids in which a target analyte (i.e., the analyte sought to be processed) is not present. For example, wash fluids (e.g., saline, etc.) may be referred to as analyte for the purposes of the present invention.

The analyte may be processed within one or more chambers formed in the processing device to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise thermal control (e.g., an isothermal process sensitive to temperature variations) and/or rapid thermal variations. More particularly, the present invention provides processing devices that include one or more process arrays, each of which may include an optional loading chamber, at least one chamber, a thermal transfer structure, and conduits for moving fluids between various components of the process arrays.

The term "chamber" as used herein should not be construed as limiting the chamber to a defined volume in which a process (e.g., PCR, Sanger sequencing, etc.) is performed. Rather, a chamber as used herein may include, e.g., a volume in which materials are loaded for subsequent delivery to another chamber as the processing device if rotated, a chamber in which the product of a process is collected, a chamber in which materials are filtered, etc.

Although various constructions of illustrative embodiments are described below, processing devices of the present invention may be similar to those described in, e.g., U.S. Patent Application Publication Nos. US2002/0064885 (Bedingham et al.); US2002/0048533 (Bedingham et al.); US2002/0047003 (Bedingham et al.), and US2003/138779 (Parthasarathy et al.); US2005/0126312 (Bedingham et al.); US2005/0129583 (Bedingham et al.); as well as U.S. Pat. No. 6,627,159 B1 (Bedingham et al.) and U.S. Pat. No. 6,987,253 B2 (Bedingham et al.). The documents identified above all disclose a variety of different constructions of processing devices that could be used to manufacture processing devices according to the principles of the present invention. The devices may preferably include fluid features designed to process discrete microfluidic volumes of fluids, e.g., volumes of 1 milliliter or less, 100 microliters or less, or even 10 microliters or less.

Although described in connection with rotating devices in which centrifugal force generated by rotation can be used to move fluids within the conduits and chambers, the methods and devices of the present invention may also be used in connection with gravitational forces (actual or induced) to move fluids in which case the device itself need not be rotated. It should, however, be understood that devices and methods of the present invention may, in some instances, rely on gravitational force and centrifugal force to move fluids through the process arrays (with the gravitational and centrifugal forces acting simultaneously or at different times)

It may be preferred that at least one of the sides of the processing device 10 present a surface that is complementary to a base plate or thermal structure apparatus as described in, e.g., U.S. Pat. No. 6,734,401 titled ENHANCED SAMPLE PROCESSING DEVICES SYSTEMS AND METHODS (Bedingham et al.); U.S. Patent Application Publication No. US 2007-0009391 A1 (Ser. No. 11/174,680), titled COMPLIANT MICROFLUIDIC SAMPLE PROCESSING DISKS; U.S. Patent Application Publication No. US 2007-0010007 A1 (Ser. No. 11/174,757), titled SAMPLE PROCESSING DEVICE COMPRESSION SYSTEMS AND METHODS; etc. In some embodiments, it may be preferred that at least one of the major sides of the processing devices of the present invention present a flat surface.

Figure 2:
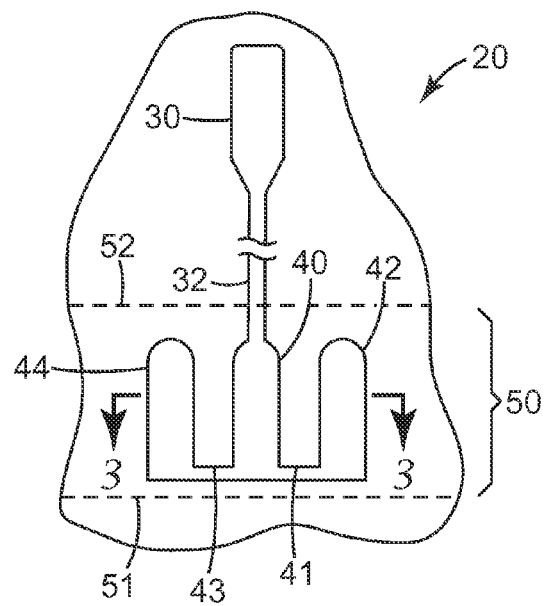
FIG. 2 is an enlarged view including one process array that may be found on the processing device of FIG. 1.

One illustrative processing device manufactured according to the principles of the present invention is illustrated in FIGS. 1 & 2, where FIG. 1 is a plan view of one exemplary processing device 10 and FIG. 2 is an enlarged view of a portion of the processing device 10 that includes a process array 20. The processing device 10 may preferably be in the shape of a circular disc as illustrated in FIG. 1, although any other shape that can be rotated could be used in place of a circular disc. It may be preferred that the processing device 10 be a self-contained, unitary article that can be separately transported apart from a system in which the processing device 10 may be used.

The processing device 10 may preferably be rotated about an axis of rotation that preferably coincides with the center 12 of the processing device 10. It may be preferred that the axis of rotation be generally perpendicular to the opposing major sides of the processing device 10, although that arrangement may not be required. In some embodiments, the center 12 of the processing device 10 may include an opening sized to receive a spindle that can extend therethrough.

The processing device 10 includes at least one, and preferably multiple process arrays 20. If the processing device 10 is circular as depicted, it may be preferred that each of the depicted process arrays 20 extends from proximate the center 12 of the processing device 10 towards the periphery of the processing device 10. The process arrays 20 may preferably be substantially radially aligned with respect to the center 12 of the processing device 10 (where "substantially radially-aligned" means generally aligned along a radius 21 extending outward from the center 12 of the processing device 10). Although this arrangement may be preferred, it will be understood that any arrangement of process arrays 20 may alternatively be used. Also, although the illustrated processing device 10 includes one process array 20, it will be understood that two or more of the process arrays 20 may be provided in the processing device 10.

The exemplary process array 20 (in the depicted embodiment) includes a loading chamber 30 connected to a chamber 40 along a conduit 32. The process array 20 also includes thermal transfer structure in the form of two thermal transfer chambers 42 and 44 connected to the chamber 40 by conduits 41 and 43 (respectively).

It should be understood that a number of the features associated with the depicted exemplary process array 20 may be optional. For example, the loading chamber 30 and associated conduit 32 may be optional where the analyte can be introduced directly into the chamber 40 directly or through a different loading structure. At the same time, additional features may be provided with the process array 20. For example, two or more loading chambers and separate conduits leading to the chamber may be associated with a process array according to the present invention. Other features may also be provided in process arrays of the present invention, such as valves, filters, beads, etc.—some of which may be described in connection with other exemplary embodiments herein.

Any loading structure provided in connection with the process array 20 may be designed to mate with an external apparatus (e.g., a pipette, hollow syringe, or other fluid delivery apparatus) to receive the analyte. The loading structure itself may define a volume (as, e.g., does loading chamber 30 of FIG. 1) or the loading structure may define no specific volume, but, instead, be a location at which analyte is to be introduced. For example, the loading structure may be provided in the form of a port through which a pipette, needle, etc. is to be inserted or attached. In one embodiment, the loading structure may be, e.g., a designated location along a conduit that is adapted to receive a pipette, syringe needle, etc. The loading may be performed manually or by an automated system (e.g., robotic, etc.). Further, the processing device 10 may be loaded directly from another device (using an automated system or manually).

Figure 3:
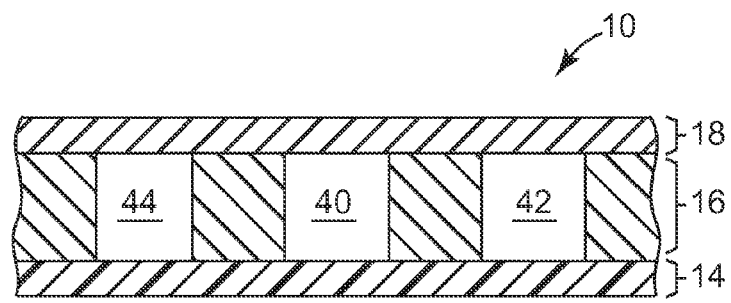
FIG. 3 is an enlarged cross-sectional view of a portion of the processing device of FIGS. 1 & 2, taken along line 3-3 in FIG. 2.

FIG. 3 is an enlarged cross-sectional view of the processing device 10 taken along line 3-3 in FIG. 2. Although processing devices of the present invention may be manufactured using any number of suitable construction techniques, one illustrative construction can be seen in the cross-sectional view of FIG. 3. The depicted processing device 10 includes a base layer 14 attached to one major surface of a core layer 16 (where a major surface is a surface that, e.g., faces a viewer in the plan view of FIG. 1). A cover layer 18 is attached to the core layer 16 over the major surface of the core layer 16 that faces away from the base layer 14.

The layers of processing device 10 may be manufactured of any suitable material or combination of materials. Examples of some suitable materials for the base layer 14 and/or core layer 16 include, but are not limited to, polymeric material, glass, silicon, quartz, ceramics, etc. For those processing devices 10 in which the layers will be in direct contact with analytes, reagents, etc., it may be preferred that the material or materials used for the layers be non-reactive with the analytes, reagents, etc. Examples of some suitable polymeric materials that could be used for the substrate in many different bioanalytical applications may include, but are not limited to, polycarbonate, polypropylene (e.g., isotactic polypropylene), polyethylene, polyester, etc.

It may be preferred that the base layer 14 and/or cover layer 18 be manufactured of materials that allow the detection of one or more characteristics of analyte in the chamber 40. Such detection may allow for qualitative and/or quantitative analysis. It may be preferred that the detection be achieved using selected light, where the term "light" refers to electromagnetic energy, whether visible to the human eye or not. It may be preferred that the light fall within a range of ultraviolet to infrared electromagnetic energy, and, in some instances, it may be preferred that light include electromagnetic energy in the spectrum visible to the human eye. Furthermore, the selected light may be, e.g., light of one or more particular wavelengths, one or more ranges of wavelengths, one or more polarization states, or combinations thereof.

Regardless of the component through which detection is to occur (e.g., the cover layer 18 and/or the base layer 14), the materials used preferably transmit significant portions of selected light. For the purposes of the present invention, significant portions may be, e.g., 50% or more of normal incident selected light, more preferably 75% or more of normal incident selected light. Examples of some suitable materials for the detection window include, but are not limited to, e.g., polypropylenes, polyesters, polycarbonates, polyethylenes, polypropylene-polyethylene copolymers, cyclo-olefin polymers (e.g., polydicyclopentadiene), etc.

In some instances, it may be preferred that the base layer 14 and/or the cover layer 18 of the processing device 10 be opaque such that the processing device 10 is opaque between the volume of the chamber 40 and at least one side of the processing device 10. By opaque, it is meant that transmission of the selected light as described above is substantially prevented (e.g., 5% or less of such normally incident light is transmitted).

The components making up processing device 10 may be attached to each other by any suitable technique or combination of techniques. Suitable attachment techniques preferably have sufficient integrity such that the attachment can withstand the forces experienced during processing of analytes in the chambers. Examples of some of the suitable attachment techniques may include, e.g., adhesive attachment (using pressure sensitive adhesives, curable adhesives, hot melt adhesives, etc.), heat sealing, thermal welding, ultrasonic welding, chemical welding, solvent bonding, coextrusion, extrusion casting, mechanical (e.g., friction-fit, etc.), etc. and combinations thereof. Furthermore, the techniques used to attach the different layers may be the same or different. For example, the technique or techniques used to attach the base layer 14 and the core layer 16 may be the same or different as the technique or techniques used to attach the cover layer 18 and the core layer 16. Some potentially suitable attachment techniques may be described in the patent documents identified herein.

Although the various layers and components in the cross-sectional views of different exemplary processing devices are depicted as homogeneous constructions, it should be understood that the various components could be constructed of more than one material/layers. Further, in some processing devices, multiple components may potentially be combined into a unitary article to reduce the number of components that must be attached to manufacture a processing device.

Figure 4A:
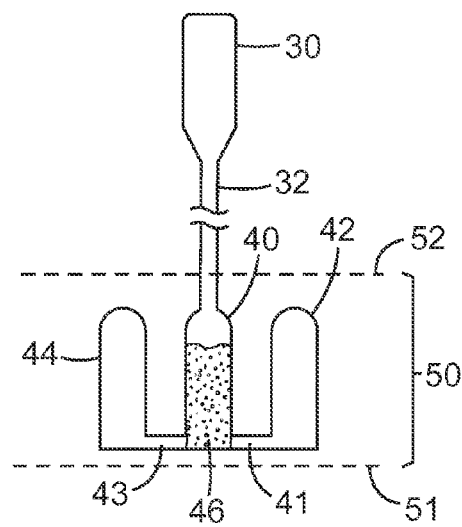
FIGS. 4A & 4B depict an exemplary process of transporting fluid using the exemplary thermal transfer structure of the process array of FIG. 2.
Figure 4B:
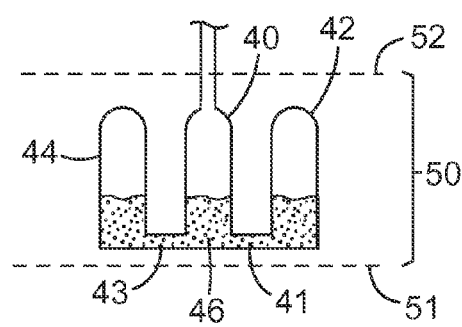

FIGS. 4A & 4B depict one exemplary process in which analyte is thermally transferred within the depicted process array. As depicted in FIG. 4A, the analyte 46 is located in the chamber 40. As discussed herein, the analyte 46 may preferably transferred into the chamber 40 from the loading chamber 30 through conduit 32. The transfer from loading chamber 30 to the chamber 40 through conduit 32 may preferably be accomplished by rotating the processing device 10 or under the influence of gravitational forces.

After the analyte 46 is in the chamber 40, transfer to the thermal transfer chambers 42 and 44 of the thermal transfer structure may preferably be accomplished by temperature control as discussed herein. Thermally-driven transfer may be required where, e.g., the dimensions of the conduits 41 and 43 are selected such that the analyte 46 in the chamber 40 is prevented from entering the thermal transfer chamber 42 and 44 as the processing device 10 is rotated to move the analyte 46 into chamber 40. In such embodiments, the physical dimensions of at least a portion of the conduits 41 & 43 may be selected such that the conduits 41 & 43 prevent flow in the absence of a pressure differential (e.g., thermally-driven vacuum) between chamber 40 and one or both of chambers 42 & 44.

Referring to FIGS. 1 and 2, the processing device 10 may preferably include a heat transfer structure 50 which, in a processing device 10 that is circular in shape, may preferably be in the form of a ring with an outer diameter 51 and an inner diameter 52. It may be preferred that the heat transfer structure 50 be in the form of, e.g., a metallic foil layer or other material that may be used to transfer thermal energy into and/or out of the chambers 40, 42 and 44. That foil layer may, in some instances, be contained within the base layer 14 of the composite structure depicted in FIG. 3.

To transfer the analyte 46 to the thermal transfer chambers 42 and 44, the temperature of the fluids resident in the chambers 42 and 44 may preferably be changed from a starting temperature to a second temperature, where the second temperature is higher than the starting temperature. As the temperature of the resident fluid is raised to the second temperature, the volume of the resident fluid in the chambers 42 and 44 increases, forcing a portion of the resident fluid from each of the chambers 42 and 44 into chamber 40 through conduits 41 and 43.

The resident fluids in the thermal transfer structures of process arrays according to the present invention may be a gas, liquid, or combination thereof. In some instances, thermal transfer may be enhanced if the resident fluid includes both a gas and a liquid (e.g., the resident fluid may include air and water). The addition of materials such as water, hydrogels, etc. that may change phase (e.g., transition between a liquid and a gas) during the thermal transfer process may enhance thermal transfer by providing a greater increase in volume when heated (as compared to heating a gas alone). The larger increase in volume of the resident fluid may provide a corresponding larger amount of vacuum to move fluids through the system as the heated gas cools (and possibly returns to the liquid phase).

This phase change-enhanced transfer may be advantageous where two or more heating/cooling cycles are used to transfer fluids. As the amount of liquid that changes phase during the process increases, the volumes of fluids moved may also preferably increase. Thus, while an initial heating/cooling cycle may result in only a small amount of fluid being transferred, each successive cycle may result in increasing amounts of fluid transfer. In essence, the initial transfer cycle may be considered as "priming" the system for more efficient transfer.

The resident fluid in the different thermal transfer chambers 42 and 44 may be the same or different. Although the resident fluid in the thermal transfer chambers 42 and 44 may include air as its gaseous component, other gases (e.g., nitrogen, etc.) may alternatively be provided in the resident fluid in the chambers 42 and 44.

After heating to the second temperature, the resident fluid in the thermal transfer chambers 42 and 44 may preferably be reduced to a third temperature that is below the second temperature. The third temperature to which the resident fluid in the chambers 42 and 44 is lowered after heating to the second temperature may be the same as the starting temperature, lower than the starting temperature, or higher than the starting temperature.

As the temperature of the resident fluid remaining in the thermal transfer chambers 42 and 44 falls toward the third temperature (from the second temperature), the volume of the resident fluid in the thermal transfer chambers 42 and 44 decreases. That decrease in volume preferably provides a vacuum (i.e., pressure differential) that draws or moves at least a portion of the analyte 46 into the thermal transfer chambers 42 and 44 (as depicted in FIG. 4B). The vacuum force may, in some instances be supplemented by gravity or centrifugal force generated by rotating the processing device 10.

In some instances, the analyte may be apportioned equally among the chamber 40 and the thermal transfer chambers 42 and 44 as depicted between FIGS. 4A & 4B (where approximately one-third of the analyte 46 as depicted in FIG. 4A is found in each of chambers 40, 42, and 44 as depicted in FIG. 4B). In other instances, the division of analyte between a chamber and any connected thermal transfer chambers may be unequal. The heating and cooling of resident fluid in the thermal transfer chambers 42 and 44 may be performed in two or more sequential heating and cooling cycles where, e.g., a single cycle of heating and cooling does not provide a desired amount of material transfer.

Heating as discussed herein may be accomplished using any suitable technique, e.g., transferring thermal energy into the resident fluid in the chambers according to the principles discussed in, e.g., U.S. Pat. No. 6,734,401 B2 (Bedingham et al.); U.S. Patent Application Publication No. US 2007-0009391 A1 (Ser. No. 11/174,680), titled COMPLIANT MICROFLUIDIC SAMPLE PROCESSING DISKS; U.S. Patent Application Publication No. US 2007-0010007 A1 (Ser. No. 11/174,757), titled SAMPLE PROCESSING DEVICE COMPRESSION SYSTEMS AND METHODS; etc. The cooling described herein may also preferably be accomplished according to the principles discussed in the above-identified documents (e.g., by convection as the processing device rotates, Peltier elements, etc.).

Figure 5:
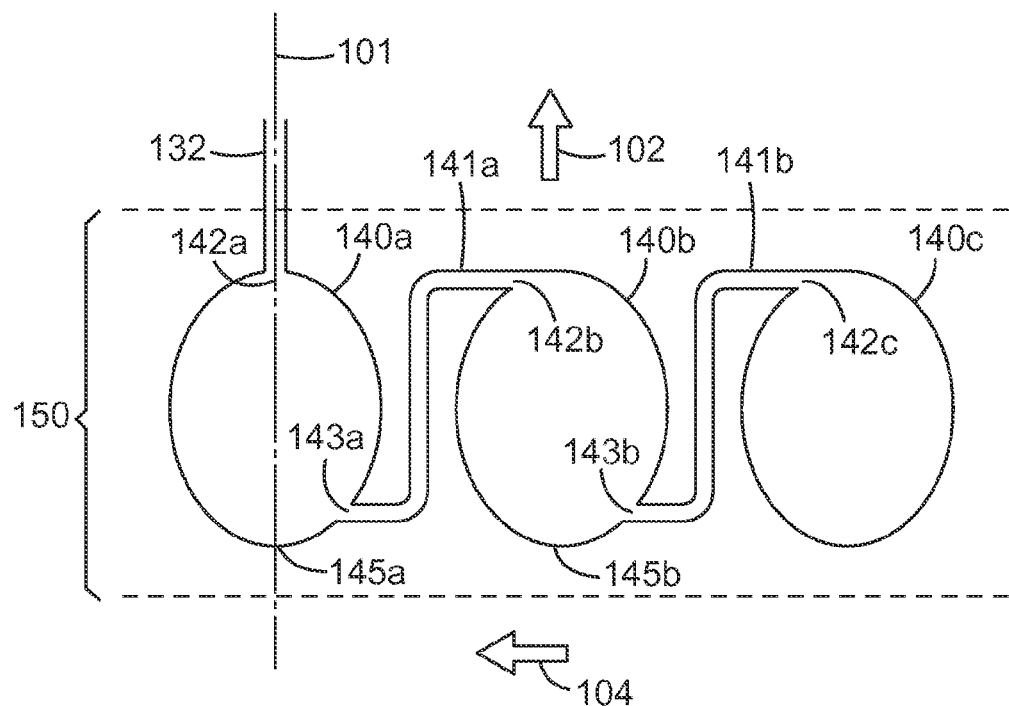
FIG. 5 is a plan view of one example of a process array including serially-connected chambers.

Another process array in which the thermal transfer principles of the present invention may be practiced is depicted in FIG. 5. The depicted process array includes a series of chambers 140a, 140b, and 140c. All or only some of the chambers may be located within a temperature-controlled portion 150 of a processing device (all of the chambers are located in the temperature-controlled portion 150 in FIG. 5). It may be preferred, e.g., that the serially-connected chambers all be located such that they are within an annular ring of a processing device that can be heated in accordance with the principles discussed in, e.g., U.S. Pat. No. 6,734,401 B2 (Bedingham et al.); U.S. patent application Ser. No. 11/174,680, titled COMPLIANT MICROFLUIDIC SAMPLE PROCESSING DISKS, filed on Jul. 5, 2005; etc. The cooling described herein may also preferably be accomplished according to the principles discussed in the above-identified documents (e.g., by convection as the processing device rotates, using compressed gases, Peltier elements, etc.).

The depicted chambers 140a, 140b, and 140c are serially connected to each other (although it may be useful to isolate the chambers with one or more valves as discussed in connection with other embodiments herein). The first chamber 140a may preferably be fed by a conduit 132 that may preferably lead from a loading chamber or other loading structure into which analyte or other fluids may be introduced into the process array. The conduit 132 enters the first chamber 140a through an inlet port 142a from, e.g., the general direction of an axis of rotation about which the processing device may be rotated to assist in processing. The axis of rotation may preferably be positioned on or near a radius 101 in the direction indicated generally by arrow 102 while the chambers 140a, 140b, and 140c travel generally in the direction of arcuate arrow 104. The direction indicated by arrow 102 may also be referred to as the upstream direction because denser fluids would tend to move in the opposite direction (which may be referred to as the downstream direction) as the device in which chambers 140 are located is rotated. Arrow 102 and the upstream direction will be understood as being opposite the force of gravity in a method/system in which rotation is not required.

In the embodiment of FIG. 5, the second and third chambers 140b and 140c form the thermal transfer structure used to effect thermal transfer in accordance with the principles of the present invention. The second chamber 140b may preferably be connected to the first chamber 140a through a transfer conduit 141a and the second chamber 140b may preferably be connected to the third chamber 140c through a transfer conduit 141b. Because thermal transfer techniques may be used to move fluids through the chambers 140a, 140b, and 140c, the chambers need not necessarily be located successively further away from the axis of rotation (or further downstream in the direction of the gravitational forces acting on the device).

As the temperature of fluids within the chambers changes, the fluids may be thermally transported between them. For example, analyte may be delivered into the first chamber 140a by, e.g., rotating the processing device containing the chamber 140a such that the analyte flows into the first chamber 140a by centrifugal acceleration. Once in the first chamber 140a, the analyte may be processed to, e.g., remove unwanted materials, amplify selected genetic material, etc.

At some point, the analyte in the first chamber 140a may preferably be transferred to the second chamber 140b through the conduit 141a connecting the first chamber 140a and the second chamber 140b. Because the conduit 141a and the second chamber 140b are located upstream or closer to the axis of rotation than the outlet port 143a through which fluid analyte enters the transfer conduit 141a, gravity or rotation of the process array alone will not be capable of transferring fluids from the first chamber 140a to the second chamber 140b. In such a situation, the thermal transfer techniques of the present invention may be used to effect fluid transfer.

With fluid analyte located in the first chamber 140a, the resident fluid in the second chamber 140b and third chamber 140c is heated to a second temperature above a starting temperature. As the temperature of the resident fluid in the second chamber 140b and third chamber 140c increases, the volume of the resident fluid increases such that a portion of the resident fluid passes into the first chamber 140a (entering through port 143a). If the heating occurs while the processing device is rotating or under the influence of gravity as discussed herein, the analyte in the first chamber 140a is driven towards the radially distal end 145a of the first chamber 140a (i.e., the end of the first chamber 140a that is located furthest from the axis of rotation). If the analyte is present at port 143a as the heated resident fluid passes into the first chamber from conduit 141a, then the resident fluid will pass through the analyte in the first chamber 140a.

After a portion of the resident fluid passes into the first chamber 140a through port 143a, the resident fluid remaining in the second chamber 140b and third chamber 140c may be cooled to a third temperature. As the resident fluid cools to the third temperature, the volume of the resident fluid in those chambers decreases, thus creating a vacuum that preferably moves or draws a portion of the analyte in the first chamber 140a into the second chamber 140b through the transfer conduit 141a.

The analyte drawn out of the first chamber 140b through conduit 141a enters the second chamber 140b through port 142b which is located at radially proximal (upstream) end of the second chamber 140b that is nearest the axis of rotation. It should be noted that transfer conduit 141a exits first chamber 140a through port 143a which is located radially distal (downstream) from port 142b through which transfer conduit 141a connects to second chamber 140b. In other words, port 142b is located closer to the axis of rotation of the processing device than port 143a.

As depicted in FIG. 5, the port 143a through which the transfer conduit 141a connects to the first chamber 140a is located closer to the axis of rotation than the distal end 145a of the first chamber 140a. In situations where a port (such as port 143a) is located closer to the axis of rotation than the downstream or radially distal end 145a of a chamber 140a, but is not located at the upstream or radially proximal end of the chamber 140a (as is port 142a), the port 143a may be described as being positioned at an "intermediate location" of the chamber (or other structure). In other words, an intermediate location along a chamber or conduit is a location that is neither closest to or furthest from the axis of rotation for the chamber or conduit in question in a rotating system and not at the upstream end or the downstream end in a non-rotating gravitational system.

Constituents with greater density (e.g., liquids, beads, etc. as generally compared to gases) will be driven toward the radially distal end 145a of the first chamber 140a as the processing device is rotated about the axis of rotation (or drawn in that direction in a gravitational system). Because the port 143a is located at an intermediate location that is closer to the upstream end than the downstream or distal end 145a of the first chamber 140a, the constituents of analyte that gather at the distal end 145a will not typically be drawn into the transfer conduit 141a (because they will be located past the port 143a in a more radially distal or downstream location).

The portion of the analyte transferred into the second chamber 140b may be transferred to the third chamber 140c by a thermal transfer process similar to that used to transfer analyte from the first chamber 140a to the second chamber 140b. In the transfer, the heated resident fluid in the third chamber 140c passes into the second chamber 140b through the transfer conduit 141b. The transfer conduit 141b opens into the second chamber 140b through port 143b on one end and opens into the third chamber 140c through port 142c on the opposite end. Similar to the transfer conduit 141a, the port 142c leading into third chamber 140c is located further upstream or closer to the axis of rotation of the processing device than port 143b (through which fluids enter the transfer conduit 141b). Further, because the port 143b is positioned at an intermediate location (e.g., closer to the axis of rotation than the distal end 145b of the second chamber 140b), the constituents of analyte that gather at the distal end 145b of second chamber 140b will not typically be drawn into the transfer conduit 141b.

When coupled with rotational processing techniques or gravity, thermal transfer of fluids within a process array can be used to accomplish more complex processing sequences not possible with known processing devices. One example of a more complex processing sequence will be described now in connection with the process array depicted in FIG. 6.

Figure 6:
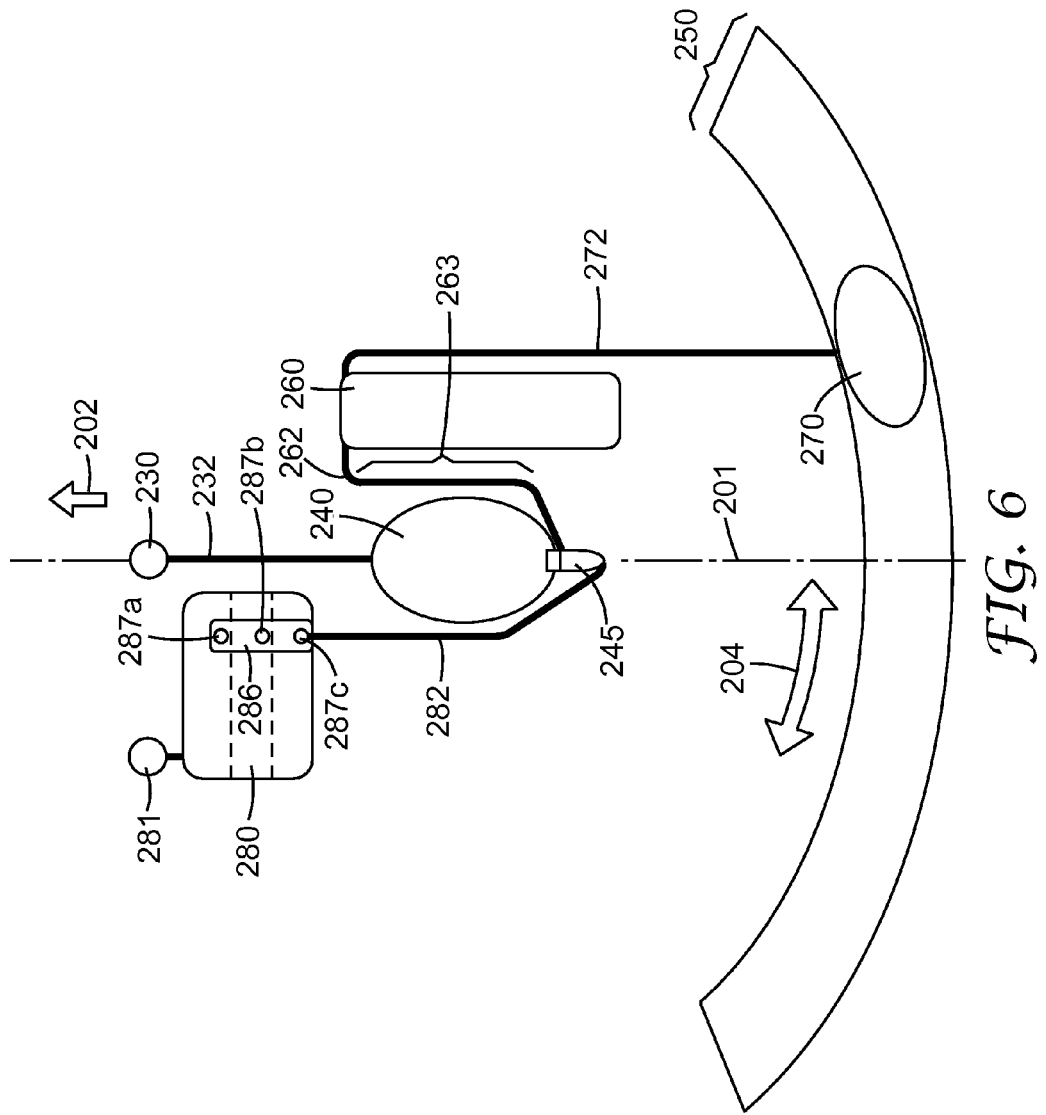
FIG. 6 is a plan view of another exemplary process array according to the present invention.

The exemplary process array of FIG. 6 is preferably provided in a processing device designed for rotation about an axis of rotation positioned on or near a radius 201 located in the direction of arrow 202. When rotated about the axis of rotation, the features of the process array will travel generally in the direction indicated by arcuate arrow 204. Alternatively, the process array of FIG. 6 may be used in a non-rotating gravity based device in which the arrow 202 is indicative of the upstream direction, i.e., is opposite of the direction of the gravitational forces acting on the process array (where the direction of the gravitational forces is the downstream direction).

The exemplary process array includes a loading structure 230 that connects with a first chamber 240 through a conduit 232. The chamber 240 includes a downstream or radially distal end 245 into which materials are driven when the processing device containing the process array is rotated about the axis of rotation or acted on by gravitational forces. As such, the terms "upstream" and "downstream" may also be used in referring to directions in connection with the process array of FIG. 6. More specifically, the direction indicated by arrow 202 may be referred to as upstream, while the opposite direction may be referred to as downstream.

The process array also includes a thermal transfer structure to assist with thermal transfer of fluids through the chamber. In the exemplary embodiment depicted in FIG. 6, the thermal transfer structure includes a trap chamber 260 in fluid communication with the chamber 240 through a transfer conduit 262. The thermal transfer structure also includes a thermal drive chamber 270 in fluid communication with the trap chamber 260 through a drive conduit 272.

The transfer conduit 262 preferably includes a fluid trap 263 in which a portion of the transfer conduit 262 travels in the upstream direction between the transfer port (where the transfer conduit connects with the chamber 240) and the trap chamber 260 (or the thermal drive chamber 270). That fluid trap 263 effectively prevents fluids from moving out of the chamber 240 to the trap chamber 260 or the thermal drive chamber 270 by rotation of the device containing the process array, under the influence of gravity, etc.

In use, the depicted thermal transfer structure can be used to transfer fluids from the chamber 240 into the trap chamber 260. The trap chamber 260 can, therefore, serve as a reservoir for fluids removed from the chamber 240. It may be preferred that the trap chamber 260 have a volume large enough to accept multiple fluid transfers from the chamber 240. The volume of the trap chamber 260 may preferably be equal to or greater than the volume of the chamber 240. In some instances, it may be preferred that the volume of the trap chamber 260 be one and one-half (1.5) times the volume of the chamber 240.

Thermal transfer of analyte may be accomplished according to the principles discussed above. One difference, however, may be found in the remote location of the thermal drive chamber 270. It may be preferred that the thermal drive chamber 270 be located in a region 250 of the processing device that is thermally controlled, e.g., a region that can be selectively heated and/or cooled. The region 250 may preferably be in the form of an annular ring (an arcuate portion of which is depicted in FIG. 6) if the processing device is in the form of a circular disc.

Although the thermal drive chamber 270 is located remote from the remainder of the process array, it is in fluid communication with the trap chamber 260 and, ultimately, the chamber 240 through conduits 272 and 262. To effect a thermally-driven transfer of fluid from the chamber 240 to the trap chamber 260, the resident fluid in the drive chamber 270 may preferably be heated so that its temperature increases from a starting temperature to a second temperature. As the temperature of the resident fluid in the drive chamber 270 increases, its volume also increases. That increase in volume forces a portion of the resident fluid in the thermal drive chamber 270 into conduit 272 which, in turn, forces a portion of the resident fluid in the conduit 272 into the trap chamber 260. Correspondingly, a portion of the resident fluid in the trap chamber 260 is forced into the transfer conduit 262. The resident fluid in the transfer conduit 262 is then forced into the chamber 240.

It may be preferred that any fluids in the chamber 240 that are to be transferred to the trap chamber 260 be located at or upstream of (e.g., closer to the axis of rotation) the point at which the transfer conduit 262 enters the chamber 240. Centrifugal and/or gravitational force may preferably drive or draw fluids in the chamber 240 towards the downstream or radially distal end 245 of the chamber 240 so that the port at which the transfer conduit 262 connects to the chamber 240 is covered by the fluid. The result is that the resident fluid forced into the chamber 240 from the conduit 262 preferably passes through the analyte in the chamber 240.

After the resident fluid in the thermal transfer structure (which, in the depicted embodiment, includes conduits 262 and 272, along with trap chamber 260 and thermal drive chamber 270) is forced into the chamber 240, the temperature of the resident fluid remaining in the thermal drive chamber 270 may preferably be reduced from the second temperature to a third temperature. As the resident fluid in the thermal drive chamber 270 cools, its volume preferably decreases, creating a vacuum that is communicated through conduit 272 to trap chamber 260 and through trap chamber 260 to transfer conduit 262. The vacuum then travels through transfer conduit 262 to the chamber 240 such that fluids present at the connection between the chamber 240 and the transfer conduit 262 is drawn into the transfer conduit 262. At least a portion of the fluid moved or drawn into the transfer conduit 262 from chamber 240 is then delivered to the trap chamber 260 where it is preferably deposited.

It may be preferred that the geometry of the trap chamber 260 along with the transfer conduit 262 and the thermal drive conduit 272 be such that fluids delivered into the trap chamber 260 from the chamber 240 remain in the trap chamber 260 and are not transferred into the thermal drive chamber 270. Isolation of the thermal drive chamber 270 from the fluids transferred into the trap chamber 260 may preserve the ability of the thermal drive chamber 270 to be used to transfer fluids into the trap chamber 260 from the chamber 240 two or more times.

It may further be preferred that materials in the trap chamber are not directly heated during the thermal transfer process. Isolation of the trap chamber 260 may be enhanced if conduits in fluid communication with the trap chamber 260 enter and/or exit the trap chamber 260 at or near its radially proximal or upstream end (i.e., the end nearest the axis of rotation). In such a construction, e.g., where the transfer conduit 262 and the drive conduit 272 connect to the trap chamber 260 at locations located on a radially proximal or upstream side of the trap chamber 260, fluids entering the trap chamber 260 (while, e.g., the processing device is being rotated or is under the influence of gravitational forces) tend to move towards a downstream or radially distal side of the trap chamber 260 (i.e., opposite the direction of arrow 202) such that a majority of the fluids (preferably substantially all of the liquids) entering the trap chamber 260 do not enter the drive conduit 272. The trap chamber 260 and/or transfer conduit 262 may also include structures (e.g., baffles, etc.) that tend to direct fluids entering the trap chamber 260 from the chamber 240 downward into the main volume of the trap chamber 260.

As with transfer conduit 262 of the process array of FIG. 6, the transfer conduit 262 also includes a fluid trap 263 in which a portion of the transfer conduit 262 travels in the upstream direction between the transfer port and the thermal drive chamber 270 (when moving from the chamber 240 towards the thermal drive chamber 270). That fluid trap 263 effectively prevents fluids from moving out of the first chamber 240 to the thermal drive chamber 270 by rotation of the device containing the process array or under the force of gravity.

It may be preferred that the fluid trap 263 reach a level that is radially proximal of the chamber 240 such that even if the chamber is completely filled with analyte, rotation of the device alone will not drive the analyte past the fluid trap 263 and into either trap chamber 260 or thermal drive chamber 270.

Other optional features depicted in the exemplary process array of FIG. 6 include a second chamber 280 that can be placed in fluid communication with the chamber 240 through a conduit 282. The conduit 282 is depicted as connecting with the chamber 240 at a radially distal point of the chamber 240.

The conduit 282 may, alternatively connect to the chamber 240 at any selected location along the radial length of the chamber 240 (where radial length is the dimension of the chamber 240 along the radius 201). The second chamber 280 may be used to supply, e.g., wash fluid to the chamber 240.

Another optional feature depicted in connection with the exemplary process array of FIG. 6 is a valve structure used to control the flow of fluid from the second chamber 280 into the conduit 282. In the depicted process array, the valve structure takes the form of a valve lip 284 (shown in FIG. 7) that extends into the volume of the second chamber 280, although any suitable alternative valve could be used in place of the depicted valve structure.

Figure 7:
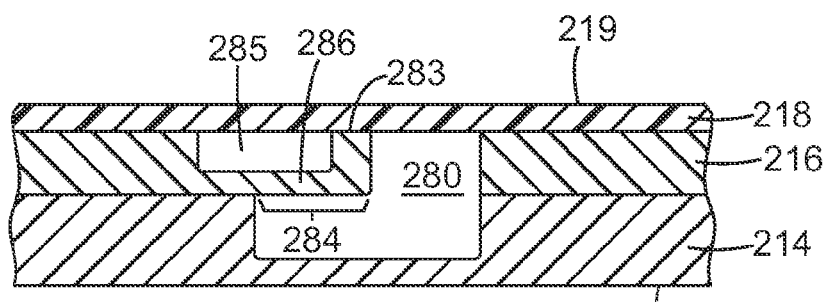
FIG. 7 is a cross-sectional view of one exemplary valve structure that may be used in connection with the process arrays of the present invention.

FIG. 7 is a cross-sectional view of the portion of the processing device containing the second chamber 280. As seen in FIGS. 6 & 7, the valve lip 284 is preferably located within the area occupied by the second chamber 280 on the processing device, i.e., the projected chamber area. The projected chamber area may preferably be defined by projecting the chamber boundaries onto either of the major sides of the processing device.

In the embodiment depicted in FIG. 7, the core layer 214 defines a first major side 215 of the processing device that faces away from a valve layer 216. The valve layer 216 is attached to the surface of the core layer 214 that faces away from the first major side 215. A cover layer 218 is attached to the surface of the valve layer 216 that faces away from the core layer 214, with the cover layer 218 defining a second major side 219 of the processing device that faces away from the first major side 215 of the processing device.

The valve lip 284 is depicted as extending into the projected chamber area as defined by the outermost boundaries of second chamber 280. Because the valve lip 284 is located within the projected chamber area, the valve lip 284 may be described as overhanging a portion of the second chamber 280 or being cantilevered over a portion of the second chamber 280.

Valve lip 284 preferably defines a valve chamber 285 that may preferably be at least partially located within the valve lip 284 as seen in FIG. 7. The valve chamber 285 is preferably in open fluid communication with the conduit 282 leading to chamber 240. As such, any fluid entering the valve chamber 285 can enter the conduit 282 for delivery to the chamber 240.

At least a portion of the valve chamber 285 may preferably be located between the second major side 219 and at least a portion of the second chamber 280. The valve chamber 285 is also preferably isolated from the second chamber 280 by a valve septum 286 separating the valve chamber 285 from the second chamber 280, such that a portion of the volume of the second chamber 280 lies between the valve septum 286 and the first major side 215 of the processing device. In the depicted embodiment, the cover layer 218 is preferably sealed to the valve lip 284 along surface 283 to isolate the valve chamber 285 from the second chamber 280.

The valve septum 286 is preferably formed of material in which openings can be formed by non-contact methods, e.g., laser ablation, focused optical heating, etc. Because such openings formed in the valve septum are typically irreversible (i.e., they cannot be closed after formation), the valve structure depicted in FIGS. 6 & 7 may be described as a "single-use" valve. The energy used to form openings in the valve septum 286 can be directed onto the valve septum 286 either through the cover layer 218 or through the core layer 214 (or through both). It may be preferred, however, that the energy be directed at the valve septum 286 through the cover layer 218 to avoid issues that may be associated with directing the energy through materials in the second chamber 280 before the energy reaches the valve septum 286.

One method of using a second chamber 280 to deliver fluids to chamber 240 of the process array of FIG. 6 will now be described. After selected fluid materials are provided in the second chamber 280, an opening can be formed in the valve septum 286 at a desired location. One example is opening 287a depicted in FIG. 6. As the processing device containing the second chamber 280 is rotated about the axis of rotation in the direction of arrow 204 or is subjected to gravitational forces, fluid in the second chamber 280 will move out of the second chamber 280 through opening 287a into the valve chamber 285 and then into conduit 282 for delivery to the chamber 240.

Because substantially all of the fluid located above the broken line extending through opening 287a will preferably move out of the second chamber 280, the location of the opening or openings formed in valve septum 286 may be selected to deliver selected volumes of fluid to the chamber 240. For example, after the initial delivery of fluid through opening 287a, a second volume of fluid in the second chamber 280 may be delivered by forming a second opening 287b in the valve septum 286. After opening 287b is provided, the discrete volume of fluid between the two broken lines extending through openings 287a and 287b may be delivered into the chamber 240. FIG. 6 also includes a third opening 287c in the valve septum 286 through which substantially all fluids in the second chamber 280 can enter the conduit 282 for delivery to the chamber 240.

The fluids to be delivered to the chamber 240 from the second chamber 280 may be provided in the second chamber 280 when the processing device is manufactured or by an end user (or an intermediate party). The fluids may be delivered directly into the second chamber 280. Alternatively, the fluids may be delivered to the second chamber through an optional loading structure 281 that is in fluid communication with the second chamber 280. The loading structure 281 may be used one or more times to deliver one or more discrete volumes of material to the second chamber 280.

One potential use for a second chamber 280 with a single-use valve structure as depicted in FIGS. 6 & 7 that is in fluid communication with chamber 240 is to provide, e.g., a wash fluid (saline, etc.) or some other fluid that may be desirably metered into the chamber 240 in one or more discrete volumes. By forming one or more openings in the valve septum 286 at one or more selected locations, discrete volumes of fluids (typically liquids) contained within the second chamber 280 can be delivered to the chamber 240 from second chamber 280.

Sequential delivery of discrete volumes from the second chamber 280 to the chamber 240 may be used to, e.g., provide a "wash" solution capable of removing undesirable materials from the chamber 240. For example, after delivery of a first volume of wash solution to chamber 240 from second chamber 280 (through, e.g., opening 287a), a portion of the wash solution with undesirable materials (in solution, entrained therein, etc.) may be removed from the chamber 240 using the thermal transfer structure (with the unwanted portion being delivered to the trap chamber 260 as described herein). Such a wash step may be repeated if a sufficient volume of wash solution is located in the second chamber 280. For example, second opening 287b may be formed to deliver a second volume of the wash solution to chamber 240.

In another exemplary method for using a process array similar to that depicted in FIGS. 6 & 7, one or more reagents may be located within the second chamber 280 (e.g., dried-down, etc.) or delivered to the second chamber 280 within a liquid such that the one or more reagents may be delivered to the chamber 240 through the conduit 282.

Figure 8:
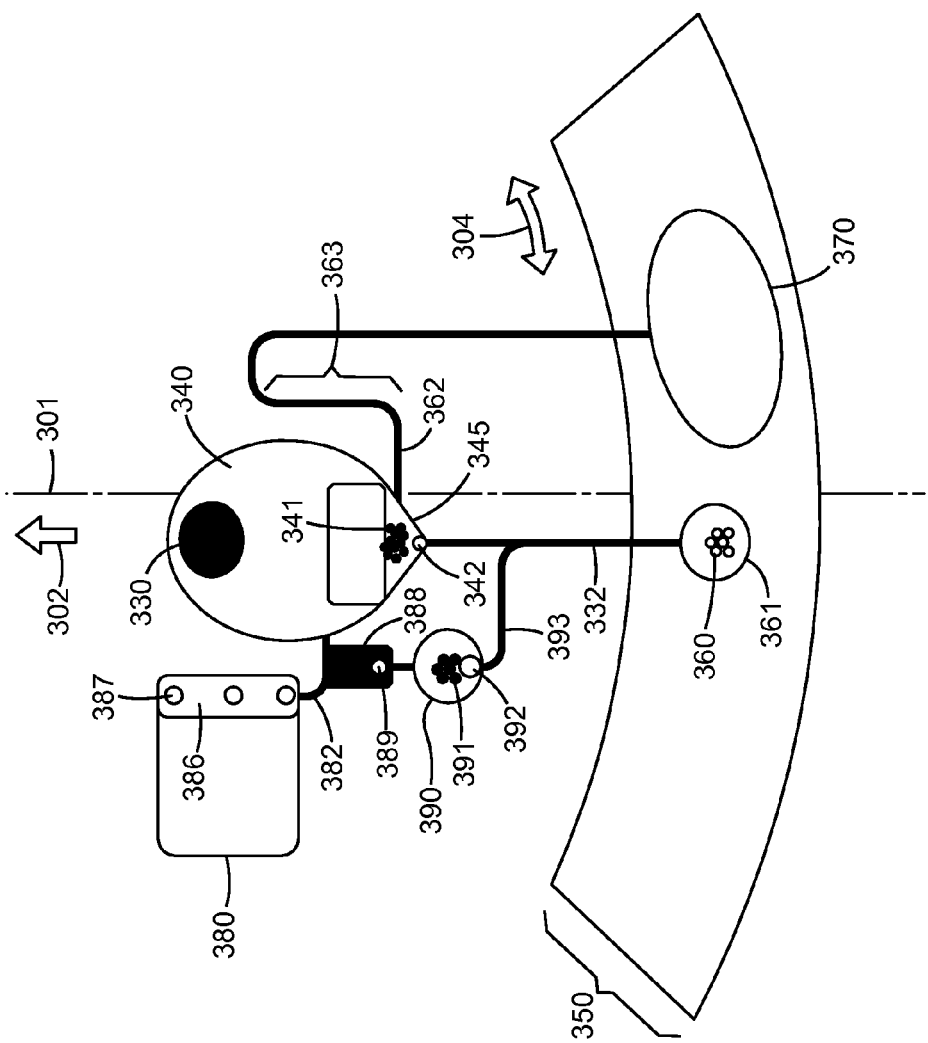
FIGS. 8-10 are plan views of other exemplary process arrays according to the present invention.

Another exemplary process array that may be provided in a processing device according to the present invention is depicted in FIG. 8. The exemplary process array of FIG. 8 is preferably provided in a processing device designed for rotation about an axis of rotation may be located on or near radius 301 in the direction of arrow 302. When rotated about the axis of rotation, the features of the process array will travel generally in the directions indicated by arcuate arrow 304. Alternatively, the process array of FIG. 8 may be used in a non-rotating gravity based device in which the arrow 302 is indicative of the upstream direction, i.e., is opposite of the direction of the gravitational forces acting on the process array (where the direction of the gravitational forces is the downstream direction).

The exemplary process array includes a first chamber 340 that connects to a second chamber 360 through a conduit 332. The first chamber 340 and the second chamber 360 may preferably be arranged on the processing device to define an upstream direction and a downstream direction. The upstream direction is the direction when moving from the second chamber 360 towards the first chamber 340 (in the general direction indicated by the arrow 302). The downstream direction is the direction when moving from the first chamber 340 towards the second chamber 360. It may be preferred that the upstream and downstream directions be substantially radially aligned with the center of the processing device in which this array is located in the case of a rotating system or aligned with gravitational forces in gravitational system.

The first chamber 340 preferably includes a single-use valve 342 that preferably prevents fluids from passing into the conduit 332 until opened. The valve 342 may take the form of an overhanging valve lip as discussed above in connection with FIG. 7. The first chamber 340 includes a radially distal or downstream end 345 into which materials move when the processing device containing the process array is rotated about the axis of rotation or is subject to gravitational forces. The first chamber 340 also preferably includes a loading structure 330 through which analyte may be introduced into the first chamber 340. In the depicted embodiment, the first chamber 340 also includes optional reagents 341 that may be used in the processing.

The second chamber 360 may preferably be located in a region 350 of the processing device that is thermally controlled, e.g., can be heated and/or cooled to change the temperature of analyte or other materials located in the second chamber 360. The region 350 may preferably be in the form of an annular ring (an arcuate portion of which is depicted in FIG. 8) if the processing device is in the form of a circular disc. As a result, the second chamber 360 may be used to process analytes that require thermal control, e.g., isothermal processes, processes requiring thermal cycling between two or more different temperatures (e.g., PCR, etc.), etc. The depicted second chamber 360 includes optional reagents 361 that may be used in connection with the processing.

The process array depicted in FIG. 8 also includes a thermal transfer structure to assist with thermal transfer of fluids through the first chamber 340. In the exemplary embodiment depicted in FIG. 8, the thermal transfer structure includes a thermal drive chamber 370 in fluid communication with the first chamber 340 through a transfer conduit 362. The thermal drive chamber 370 may preferably be positioned within thermally-controlled region 350 on the processing device.

In use, the depicted thermal transfer structure can be used to transfer fluids from the first chamber 340 into the transfer conduit 362 and the drive chamber 370. The thermal drive chamber 370 may, therefore, serve as a reservoir for fluids removed from the first chamber 340 (as well as providing the resident fluid that is used to perform the thermal transfer). It may be preferred that the thermal drive chamber 370 have a volume large enough to accept multiple fluid transfers from the first chamber 340. The volume of the thermal drive chamber 370 may, e.g., preferably be equal to or greater than the volume of the first chamber 340.

Thermal transfer of analytes (or other fluids) may be accomplished according to the principles discussed above in connection with the process array depicted in FIG. 6. As with transfer conduit 262 of the process array of FIG. 6, the transfer conduit 362 also includes a fluid trap 363 in which a portion of the transfer conduit 362 travels in the upstream direction between the transfer port and the thermal drive chamber 370 (when moving from the first chamber 340 towards the thermal drive chamber 370). That fluid trap 363 effectively prevents fluids from moving out of the first chamber 340 to the thermal drive chamber 370 by rotation of the device containing the process array or under the influence of gravitational forces.

It may be preferred that the fluid trap 363 reach a level that is radially above (i.e., closer to the axis of rotation or upstream of) the levels of any fluids located in chamber 340 such that rotation of the device (or gravity) alone will not drive the analyte in the chamber 340 past the fluid trap 363 and into thermal drive chamber 370. The height of the fluid trap 363 may vary depending on a variety of factors including, e.g., the maximum height of the fluids in the chamber 340, the size of the transfer conduit 362, the hydrophobicity/hydrophilicity of the materials used to construct the process array, etc.

It may be preferred that the fluid trap 363 reach a height (measured in the upstream direction from the radially distal or downstream end 345 of the chamber 340) that is at least 25% or more of the height of the chamber 340 (where the height of the chamber 340 is measured from its radially distal or downstream end 345 to its radially proximal or upstream end—i.e., the end located closest to the axis of rotation). Alternatively, the fluid trap 363 in the transfer conduit 362 may preferably reach a height that is at least 50% or more of the height of the chamber 340. In still another alternative, the fluid trap 363 in the transfer conduit 362 may preferably reach a height that is at least 75% or more of the height of the chamber 340. In yet another alternative, the fluid trap 363 in the transfer conduit 362 may preferably reach a height that is at least 90% or more of the height of the chamber 340.

It may be preferred that any fluids to be transferred out of the first chamber 340 be located in chamber 340 at or upstream of (i.e., closer to the axis of rotation) the transfer port at which the transfer conduit 362 connects to the first chamber 340. If the processing device is rotating about an axis of rotation as discussed above while the valve 342 is closed, centrifugal force will drive fluids in the first chamber 340 towards the radially distal or downstream end 345 of the first chamber 340 so that the transfer port at which the transfer conduit 362 connects to the first chamber 340 is covered by the fluid. If the system is not rotating, gravitational forces may be used to move fluids towards the downstream end 345 of the first chamber 340. The result is that any resident fluid forced into the first chamber 340 from the transfer conduit 362 preferably passes through the analyte in the second chamber 340.

FIG. 8 shows the location of the inlet port of the transfer conduit 362 into the side of the input chamber 340. After pipetting, when the process array of FIG. 8 is stopped or slow down, the fluid meniscus may move up (i.e., in the direction of arrow 302) by surface energy, with the fluid meniscus extending over the input port into the transfer conduit 362. In that situation, fluids in the input chamber 340 may move into the transfer conduit 362 by capillary action (i.e. the lateral surface of the fluid curves upward in the chamber 340). An alternative location for the input port leading into the transfer conduit 362 would be more central in the chamber 340 (i.e., in the direction of arrow 302), such that when the rotation slows down the surface energy would pull the fluid meniscus away from the input port leading to the transfer conduit 362.

It may, in some embodiments, be desirable to maintain a small amount of heat in the thermal drive chamber 370 when the rotation is slowed or stopped. This could potentially provide a positive outward pressure to prevent or reduce the likelihood of unwanted fluid from entering the transfer conduit 362.

In still other embodiments, it may be desirable to place an expansion chamber in the upward section of the fluid trap channel 363 (i.e., the section of the trap channel 363 furthest in the direction of arrow 302) to collect any fluid that may have entered the trap channel 363 when the rotation was stopped or slowed down. When the rotation resumes, the fluid collected in any such expansion chamber would then be driven back into the input chamber 340. Additionally, the expansion chamber or other geometries in the fluid trap channel 363 may also function to separate the continuity of the fluid channel by introducing air gap that can assist in preventing or at least halting unwanted capillary flow and siphoning of fluid from the input chamber 340.

The meniscus height, drain height, channel dimensions, fluid viscosity, fluid contact angle, rotational acceleration, differential pressure, fluid velocity and fluid density may all contribute to control the priming and siphoning of the input chamber 340 into the thermal drive chamber 370. When the process array of FIG. 8 is rotating, once the transfer conduit 362 and fluid trap 363 sections are filled with fluid below the surface of the fluid in the input chamber 340, the fluid in the input chamber 370 will empty due by siphoning. Thus the fluid drive chamber 370 fills by differential pressure and by siphoning.

Other optional features depicted in the exemplary process array of FIG. 8 include a third chamber 380 that can be placed in fluid communication with the first chamber 340 through a conduit 382. The conduit 382 is depicted as connecting with the first chamber 340 at an intermediate point of the first chamber 340. The conduit 382 may, 25 alternatively connect to the first chamber 340 at any selected location along the height of the chamber 340 (where the height of the chamber is determined between its upstream and downstream ends).

Another optional feature depicted in connection with the exemplary process array of FIG. 8 is a single-use valve structure 386 used to control the flow of fluid from the third chamber 380 into the conduit 382. In the depicted process array, the valve structure takes the form of a valve lip that extends into the volume of the third chamber 380, with the valve lip including a valve septum through which openings 387 may be formed to allow fluid to flow from the third chamber 380 into the conduit 382 (similar to the valve structure described in connection with the process array depicted in FIG. 6).

In addition to the third chamber 380, the process array may also include a subchamber 388 in which fluid from the third chamber 380 may collect during use. The fluid that collects in subchamber 388 may be delivered into an intermediate chamber 390. Control over delivery of fluid to the intermediate chamber 390 may be provided by single-use valve 389.

For example, when valve 389 is opened (after subchamber 388 is filled with a fluid), fluid from subchamber 388 can enter intermediate chamber 390 which may preferably contain one or more reagents 391. The reagents 391 may preferably interact with or be taken up by the fluid from the subchamber 388. At a selected time, a single-use valve 392 in intermediate chamber 390 may be opened. When the valve 392 is opened, the fluids in the intermediate chamber may be delivered to the second chamber 360 through conduit 393 which is in fluid communication with process conduit 332.

Figure 9:
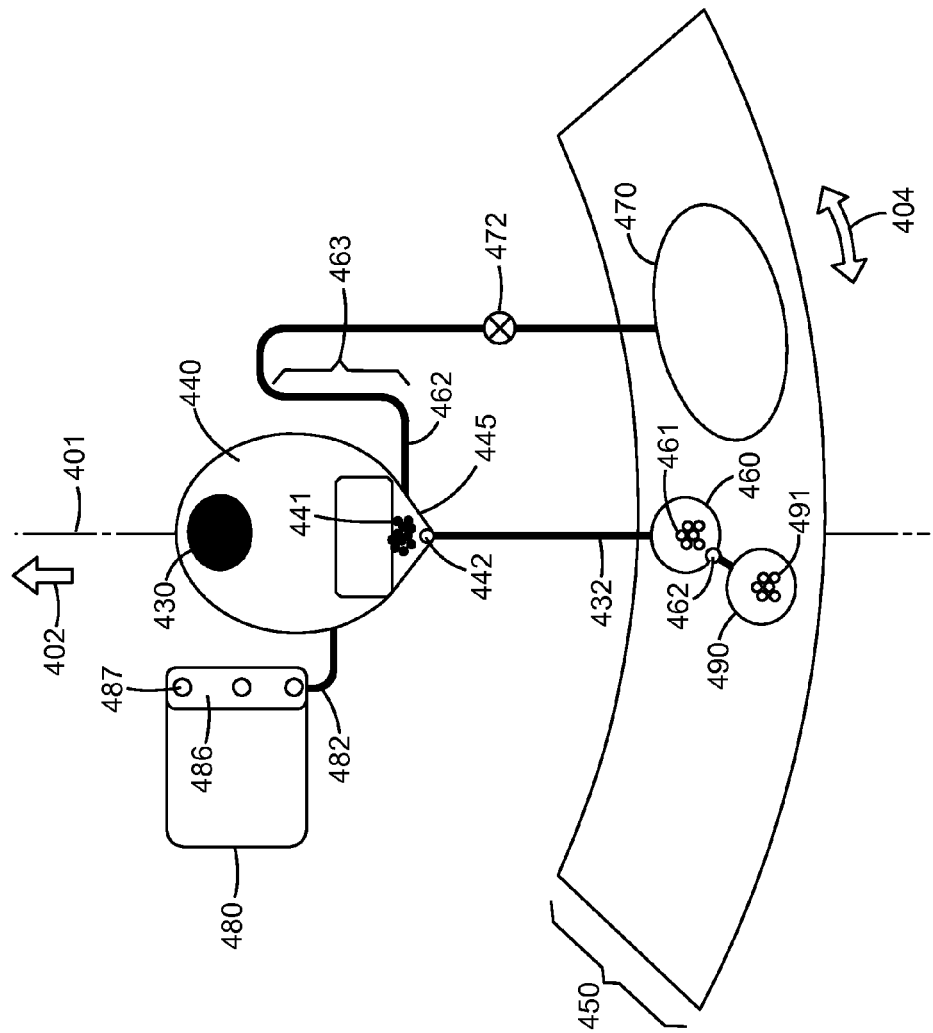

Still another exemplary process array that may be provided in a processing device according to the present invention is depicted in FIG. 9. The exemplary process array of FIG. 9 is preferably provided in a processing device designed for rotation about an axis of rotation may be located on or near radius 401 in the direction of arrow 402. When rotated about the axis of rotation, the features of the process array will travel generally in the directions indicated by arcuate arrow 404. Alternatively, the process array of FIG. 9 may be used in a non-rotating gravity based device in which the arrow 402 is indicative of the upstream direction, i.e., is opposite of the direction of the gravitational forces acting on the process array (where the direction of the gravitational forces is the downstream direction).

The exemplary process array of FIG. 9 is similar in many respects to the process array depicted in FIG. 8 and includes features such as a first chamber 440, reagents 441, loading structure 430, single-use valve 442 and downstream end 445 that are found in the first chamber 340. In addition, the process array of FIG. 9 also includes a second chamber 460 connected to the first chamber 440 by a process conduit 432, as well as a third chamber 480 and valve structure 486 through which openings 487 may be formed to deliver fluids to the first chamber 440 through conduit 482.

Also similar to the process array of FIG. 8, the process array of FIG. 9 also includes a transfer conduit 462 that connects a thermal drive chamber 470 to the first chamber 440. Thermal drive chamber 470 is preferably located within a thermally-controlled region of the processing device in which the process array is located to provide the thermal control needed to effect thermal transfer in accordance with the principles of the present invention. The transfer conduit 462 include a fluid trap 463 to prevent movement of fluid from the first chamber 440 to the thermal drive chamber 470 through rotation of the processing device or gravitational forces alone.

An additional feature depicted in the process array of FIG. 9 is the valve 472 located along the transfer conduit 462. The valve 472 may be used to control activation of the thermal transfer function. For example, if the valve 472 is closed, heating or cooling of the resident fluid in the thermal drive chamber 470 will not function to pull or move fluids from the first chamber 440. The exact location of the valve 472 is unimportant—it must merely be located between the first chamber 440 and the thermal drive chamber 470. The valve 472 may be a single-use valve similar to those described herein.

Another difference between the process array of FIG. 9 and the process array of FIG. 8 is that the process array of FIG. 9 does not include the subchamber and intermediate chamber of the process array of FIG. 8. The process array of FIG. 9 does, however, include a third chamber 490 located within the thermally-controlled region 450 as is second chamber 460. Second chamber 460 includes optional reagents 461 located therein. The third chamber 490 also includes optional reagents 491 located therein. The third chamber 490 is also connected to the second chamber 460 through single-use valve 462 and conduit 492. Rotation of the processing device in which the process array of FIG. 9 is located or gravitational forces will preferably move fluids from the second chamber 460 to the third chamber 490 where, as here, the third chamber 490 is located downstream of the second chamber 460.

Figure 10:
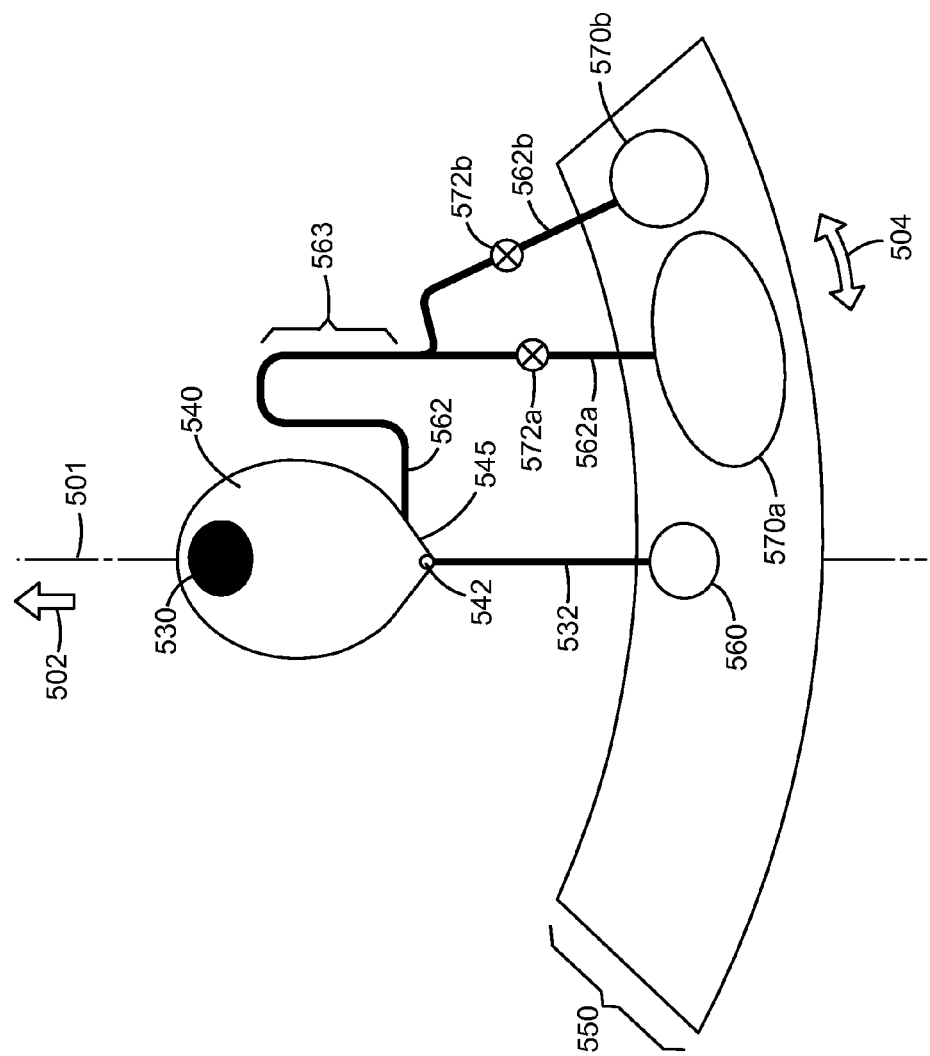

Yet another exemplary process array is depicted in connection with FIG. 10 and illustrates another optional feature in process arrays of the present invention. The exemplary process array of FIG. 10 is preferably provided in a processing device designed for rotation about an axis of rotation may be located on or near radius 501 in the direction of arrow 502. When rotated about the axis of rotation, the features of the process array will travel generally in the directions indicated by arcuate arrow 504. Alternatively, the process array of FIG. 10 may be used in a non-rotating gravity based device in which the arrow 502 is indicative of the upstream direction, i.e., is opposite of the direction of the gravitational forces acting on the process array (where the direction of the gravitational forces is the downstream direction).

The exemplary process array of FIG. 10 is similar in many respects to the process array depicted in FIGS. 8 & 9 and includes features such as a first chamber 540, loading structure 530, single-use valve 542 and downstream end 545 that are found in the first chamber 540. In addition, the process array of FIG. 10 also includes a second chamber 560 connected to the first chamber 540 by a process conduit 532.

Also similar to the process arrays of FIGS. 8 & 9, the process array of FIG. 10 also includes a transfer conduit 562 that connects the first chamber 540 to a pair of thermal drive chambers 570a and 570b. The transfer conduit 562 includes a fluid trap 563 after which the transfer conduit 562 splits into transfer conduits 562a and 562b. Both of the thermal drive chambers 570a and 570b are preferably located in the thermally-controlled region 550.

Each of the transfer conduits 562a and 562b may preferably include a valve 572a and 572b (respectively) to control flow of fluids into and out of the thermal drive chambers 570a and 570b. The valves 572a and 572b may preferably take the form of single-use valves as described herein. In some instances, one of the thermal drive chambers may not be isolated from the first chamber 540 by a valve, with additional thermal drive chambers isolated using valves. Further, although only two thermal drive chambers are depicted in the process array of FIG. 10, three or more thermal drive chambers may be provided if so desired. In another variation, where multiple thermal drive chambers are provided, each thermal drive chamber may be connected to the chamber 540 using a dedicated transfer conduit (in place of splitting the conduit 562 as depicted in FIG. 10).

The use of reagents in connection with the process arrays in processing devices of the present invention is optional, i.e., processing devices of the present invention may or may not include any reagents in the process array chambers. In another variation, some of the chambers in different process arrays may include a reagent, while others do not. In yet another variation, different chambers may contain different reagents. Further, the interiors of the chamber structures may be coated or otherwise processed to control the adhesion of reagents.

The process arrays used in processing devices of the present invention may preferably be "unvented." As used in connection with the present invention, an "unvented process array" is a process array (i.e., at least two connected chambers) in which the only openings leading into the process array are located in the loading structure, e.g., a loading chamber. In other words, to reach a chamber in the process array of an unvented process array, analytes must be delivered to the loading structure or directly into a chamber. Similarly, any air or other fluid located within the process array before loading of the analyte must also escape from the process array through the loading structure. In contrast, a vented process array would include at least one opening outside of the loading structure. That opening would allow for the escape of any air or other fluid located within the process array before loading.

Moving analyte through processing devices that include unvented process arrays may be facilitated (in addition to the thermal transfer techniques descried herein) in rotating systems by alternately accelerating and decelerating the device during rotation, essentially burping the analytes through the conduits and chambers. The rotating may be performed using at least two acceleration/deceleration cycles, i.e., an initial acceleration, followed by deceleration, second round of acceleration, and second round of deceleration. It may further be helpful if the acceleration and/or deceleration are rapid. The rotation may also preferably only be in one direction, i.e., it may not be necessary to reverse the direction of rotation during the loading process. Such a loading process allows analytes to displace the air in those portions of the process arrays that are located farther from the center of rotation of the device. The actual acceleration and deceleration rates may vary based on a variety of factors such as temperature, size of the device, distance of the analyte from the axis of rotation, materials used to manufacture the devices, properties of the analytes (e.g., viscosity), etc.

Although not depicted, the chambers in process arrays of the present invention may also include one or more optional mixing chambers to assist with mixing of materials in the chamber. Mixing chambers and their operation in a rotating processing device may be described in more detail in, e.g., U.S. Patent Application Publication No. US 2005-0129583 A1, titled SAMPLE MIXING ON A MICROFLUIDIC DEVICE, filed on Dec. 12, 2003. Briefly, however, mixing chambers provided in connection with a chamber in a rotating processing device may operate by changing the rotational speed of the processing device to move analyte in the chamber into and out of the mixing chamber to achieve mixing of the analyte.

Figure 11:
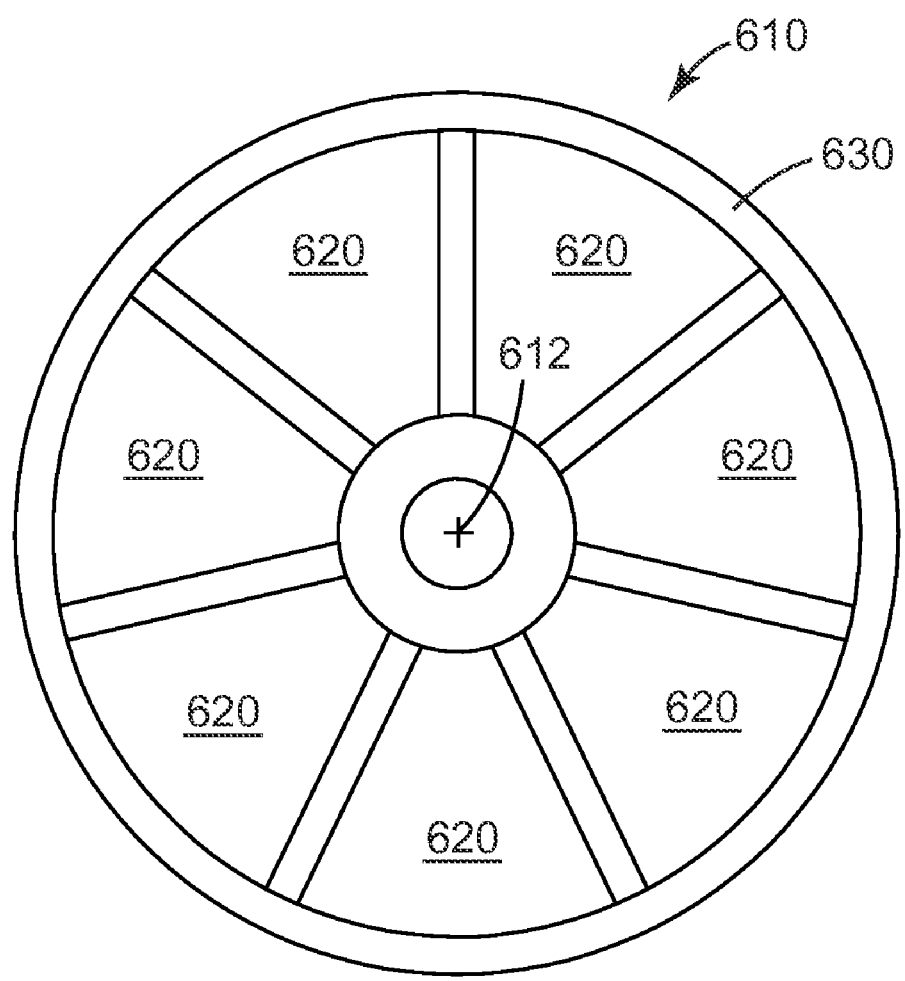
FIG. 11 depicts a modular processing device that may be used in connection with the present invention.

Yet another variation in processing devices of the present invention is depicted in FIG. 11 in which the processing device 610 is constructed from a plurality of process modules 620 that are located within a frame 630. The frame 630 may preferably define a center 612, with the process modules 620 provided in a radial array about the center 612. Each of the process modules 620 may include one or more process arrays formed therein. Further details regarding some potentially useful process modules and frames may be found in U.S. Patent Application Publication No. US 2007-0007270 A1 (Ser. No. 11/174,756), entitled MODULAR SAMPLE PROCESSING APPARATUS KITS AND MODULES, filed on Jul. 5, 2005.

As used herein and in the appended claims, the singular forms "a," "and," and "the" include plural referents unless the context clearly dictates otherwise. Thus, for example, reference to "a thermal drive chamber" includes a plurality of thermal drive chambers (unless otherwise expressly indicated) and reference to "the chamber" includes reference to one or more chambers and equivalents thereof known to those skilled in the art.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A processing device comprising:
   at least one process array formed in a body, wherein the at least one process array comprises:
      a first chamber;
      a second chamber;
      a process conduit extending between the first chamber and the second chamber;
      a thermal transfer structure comprising a thermal drive chamber containing resident fluid and a transfer conduit extending between the first chamber and the thermal drive chamber, wherein the transfer conduit enters the first chamber through a transfer port, and wherein the transfer conduit comprises a fluid trap in which a portion of the transfer conduit travels in an upstream direction between the transfer port and the thermal drive chamber; and
   a layer coupled to the body that at least partially defines the at least one process array, the layer comprising
      a heat transfer structure that defines at least a portion of the thermal drive chamber and is formed of a different material than the remainder of the base layer to transfer thermal energy into and/or out of the thermal drive chamber.

2. A device according to claim 1, wherein the fluid trap of the transfer conduit reaches at least a midpoint of the first chamber between the first chamber and the thermal drive chamber.

3. A device according to claim 1, further comprising a valve located between the first chamber and the thermal drive chamber, wherein fluid passage between the first chamber and the thermal drive chamber through the transfer conduit is prevented until the valve is opened.

4. A device according to claim 1, wherein the thermal transfer structure further comprises a trap chamber located along the transfer conduit between the first chamber and the thermal drive chamber, wherein the trap chamber is located within the fluid trap or between the fluid trap and the thermal drive chamber.

5. A device according to claim 4, wherein the trap chamber is connected to the transfer conduit along an upstream end of the trap chamber.

6. A device according to claim 1, wherein the thermal transfer structure comprises two or more thermal drive chambers, wherein all of the two or more thermal drive chambers are located downstream of the fluid trap in the transfer conduit.

7. A device according to claim 6, further comprising a valve located between the first chamber and each of the thermal drive chambers, wherein fluid passage between the first chamber and each of the thermal drive chambers through the transfer conduit is prevented until the valve located between the first chamber and the thermal drive chamber is opened.

8. A device according to claim 1, wherein the process conduit connects to the first chamber in a location downstream from the transfer port.

9. A device according to claim 1, further comprising a valve located between the first chamber and the process conduit, wherein fluid passage from the first chamber to the second chamber through the process conduit is prevented until the valve is opened.

10. A device according to claim 1, wherein a plurality of the process arrays are located in the body, wherein the process arrays are substantially radially aligned about a center of the body.

11. A device according to claim 1, wherein the heat transfer structure is formed of a metallic foil.

12. A device according to claim 10, wherein the heat transfer structure is in the form of a ring.

13. A device according to claim 12, wherein the plurality of thermal drive chambers is located within the ring.

* * * * *

UNITED STATES PATENT AND TRADEMARK OFFICE
CERTIFICATE OF CORRECTION

| | | |
|---|---|---|
| PATENT NO. | : 8,128,893 B2 | |
| APPLICATION NO. | : 11/962703 | |
| DATED | : March 6, 2012 | |
| INVENTOR(S) | : William Bedingham | |

It is certified that error appears in the above-identified patent and that said Letters Patent is hereby corrected as shown below:

Column 5
Line 67, Delete "times)" and insert -- times). --, therefor.

Column 19
Line 47, After "may," delete "25".

Column 22
Line 11, Delete "descried" and insert -- described --, therefor.

Signed and Sealed this
Fifth Day of June, 2012

David J. Kappos
*Director of the United States Patent and Trademark Office*